United States Patent [19]

Holmgren et al.

[11] Patent Number: 5,114,895

[45] Date of Patent: May 19, 1992

[54] ALUMINA CLAY COMPOSITIONS

[75] Inventors: Jennifer S. Holmgren, Bloomingdale; Stanley A. Gembicki, Clarendon Hills; Michael W. Schoonover, Arlington Heights; Joseph A. Kocal, Gurnee, all of Ill.

[73] Assignee: UOP, Des Plaines, Ill.

[21] Appl. No.: 632,244

[22] Filed: Dec. 20, 1990

Related U.S. Application Data

[63] Continuation-in-part of Ser. No. 483,844, Feb. 22, 1990, abandoned.

[51] Int. Cl.$^5$ ............................................. B01J 21/16
[52] U.S. Cl. ......................................... 502/84; 502/8; 502/72; 502/80
[58] Field of Search .......................... 502/8, 72, 80, 84

[56] References Cited

U.S. PATENT DOCUMENTS

| | | | |
|---|---|---|---|
| 2,620,314 | 2/1952 | Hoekstra | 252/448 |
| 3,609,103 | 9/1971 | Gladrow et al. | 502/68 |
| 3,639,273 | 2/1972 | Houston et al. | 502/84 |
| 3,676,330 | 7/1972 | Plank et al. | 502/64 |
| 3,965,043 | 6/1976 | Stridde | 252/455 R |
| 3,979,331 | 9/1976 | Stridde | 252/441 |
| 4,499,195 | 2/1985 | Wheelock | 502/63 |
| 4,499,319 | 2/1985 | Ballantine et al. | 585/467 |
| 4,587,009 | 5/1986 | Wheelock | 208/111 |
| 4,605,806 | 8/1986 | Ballantine et al. | 585/467 |
| 4,749,676 | 6/1988 | Blumenthal et al. | 502/251 |

OTHER PUBLICATIONS

J. M. Adams, *Applied Clay Science*, 2, pp. 309-243 (1987).
Tsuitida and Kobayashi, J. Chem. Soc. Japan (Pure Chem. Sect.) 64, 1268 (1943).
Inoue, Osugi and Kanaji, J. Chem. Soc. Japan (Ind. Chem. Sec.) 61, 407 (1958).
International Patent No. WO 88/06488.

*Primary Examiner*—Anthony McFarlane
*Attorney, Agent, or Firm*—Thomas K. McBride; Eugene I. Snyder; Frank S. Molinaro

[57] ABSTRACT

This invention relates to a composition, a method of preparing the composition and a catalyst using the composition. The composition consists essentially of a layered clay homogeneously dispersed in an inorganic oxide matrix. The clay is dispersed in such a way that the clay layers are completely surrounded by the inorganic oxide matrix. The inorganic oxide is selected from the group consisting of alumina, titania, silica, zirconia, $P_2O_5$ and mixtures thereof. The clay can be a natural clay such as montmorillonite, a metal exchanged clay ($Fe^{+3}$ exchanged) or a pillared clay such as aluminum chlorohydrate (ACH) pillared clay. The composition can be used as a catalyst for alkylation or hydrocracking or metals can be dispersed on it to provide a catalyst which is also useful for hydrocracking or alkylation.

28 Claims, 2 Drawing Sheets

ALUMINA CLAY COMPOSITIONS

CROSS-REFERENCE TO RELATED APPLICATION

This application is a Continuation-in-part of prior copending application Ser. No. 07/483,844 filed Feb. 22, 1990, now abandoned.

BACKGROUND OF THE INVENTION

Naturally occurring clays such as smectites, vermiculites and bentonites are composed of semicrystalline aluminosilicate layers (lamellae) held together by Van der Waals and electrostatic forces. Anionic charges on the siliceous layers are neutralized by cations in the interlamellar spaces. These cations, usually $Na^+$, $Ca^{+2}$, can be ion exchanged with large inorganic cations such as $Fe^{+3}$, $Cr^{+3}$ or with metal hydroxy polymer cations such as $[Al_{13}O_4(OH)_{24}(H_2O)_{12}]^{+7}$ or $[Zr(OH)_{2.4}H_2O]_4^{8+}$. The polymeric cations act as pillars, propping the clay layers apart.

Pillard clays are known to catalyze numerous reactions such as alkylation, cracking, ester formation, dimerization, oligomerization, etc. A review of the reactions catalyzed by pillared clays may be found in an article by J. M. Adams, *Applied Clay Science*, 2, pp. 309-342(1987). Of these reactions, alkylation has received considerable attention. For example, U.S. Pat. No. 4,499,319 discloses layered clays such as montmorillonite which have been ion-exchanged with metal cations such as chromium and aluminum, which are used to alkylate aromatic compounds. Other examples include U.S. Pat. No. 4,605,806 which discloses a hydrogen ion-exchanged pillared clay; U.S. Pat. No. 3,965,043 discloses a metallic cation exchanged trioctahedral 2:1 layer-lattice smectite-type clay and U.S. Pat. No. 3,979,331 which discloses a metallic cation exchanged synthetic hectorite-type clay useful for alkylating aromatic hydrocarbons.

Another reference is U.S. Pat. No. 4,499,195 which discloses a co-gel of a smectite clay with an inorganic metal oxide to produce a co-gel. The inorganic oxides include Group IV-B metal oxides and other oxides such as silicon, aluminum, thorium and uranium. However, since the metal oxide gel is stated to be formed before addition of the clay, it appears that the clay is not homogeneously dispersed in the metal oxide gel. A continuation-in-part of the '195 reference (U.S. Pat. No. 4,587,009) discloses the use of the co-gel for hydrogenation of hydrocarbons.

U.S. Pat. No. 4,111,846 discloses a catalyst that contains a zeolite as the active material and a clay as a "weighting" agent. Apparently what is meant by a "weighting" agent is a filler which is used to increase the density of the catalyst. Finally, U.S. Pat. No. 4,844,790 discloses a delaminated clay. The patentee, in passing, states that the catalyst may include a zeolite and/or a refractory oxide component as part of the catalyst. The catalyst is prepared by spray drying.

In contrast to this prior art, applicants have prepared a composition which contains a clay (pillared or nonpillared) homogeneously dispersed in an inorganic oxide matrix. The inorganic oxides which may be used as the matrix material include alumina, titania, silica, zirconia, $P_2O_5$ and mixtures thereof. A preferred method of preparing the composition involves dispersing the clay in a sol of the element which is the precursor of the oxide, thereby providing a mixture which can be formed into particles such as spheres by methods such as oil dropping, followed by calcination to form a metal oxide matrix with a clay dispersed therein. The composition has increased activity versus an untreated clay.

As will be discussed more fully herein, the inorganic oxide matrix completely surrounds the clay layers such that they are delaminated and truly homogeneously dispersed, on a one micron scale, throughout the inorganic oxide matrix. It is the use of a hydrosol which gives rise to this homogeneity which cannot be obtained by extruding or spray drying physical mixtures of a clay and a metal oxide. In fact, applicants have found that a composition of the present invention containing an acid washed montmorillonite clay in an alumina matrix has better activity than a physical mixture of the clay and alumina.

SUMMARY OF THE INVENTION

This invention relates to a composition, a method of preparing the composition, a catalyst using the composition, and a process using the composition. Accordingly one embodiment of the invention is a composition consisting essentially of a layered clay homogeneously dispersed in an inorganic oxide matrix, such that the clay layers are completely surrounded by the inorganic oxide matrix, the inorganic oxide selected from the group consisting of alumina, titania, silica, zirconia, $P_2O_5$ and mixtures thereof.

Another embodiment of the invention is a catalyst comprising a support having dispersed thereon a metal selected from the group consisting of Group IIIA, IIIB, IVB, VIII metals, molybdenum, tungsten and mixtures thereof, the support consisting essentially of a layered clay homogeneously dispersed in an inorganic oxide matrix, such that the clay layers are completely surrounded by the inorganic oxide matrix, the inorganic oxide selected from the group consisting of alumina, titania, silica, zirconia, $P_2O_5$ and mixtures thereof.

Yet another embodiment of the invention is a method of preparing a composition consisting essentially of a layered clay homogeneously dispersed in an inorganic oxide matrix, the method comprising mixing a layered clay with a hydrosol of a precursor of the inorganic oxide, forming spherical particles from said clay containing hydrosol and calcining said particles to form a composition consisting essentially of a layered clay homogeneously dispersed in an inorganic oxide matrix, such that the clay layers are completely surrounded by the inorganic oxide matrix.

Other objects and embodiments will become more apparent after a more detailed description of the invention.

BRIEF DESCRIPTION OF THE DRAWINGS

FIG. 1b is a SEM photograph showing the aluminum distribution of the extrudate sample of FIG. 1a.

FIG. 2b is a SEM photograph showing the aluminum distribution of the sphere sample of FIG. 2a.

DETAILED DESCRIPTION OF THE INVENTION

Figure 1A:
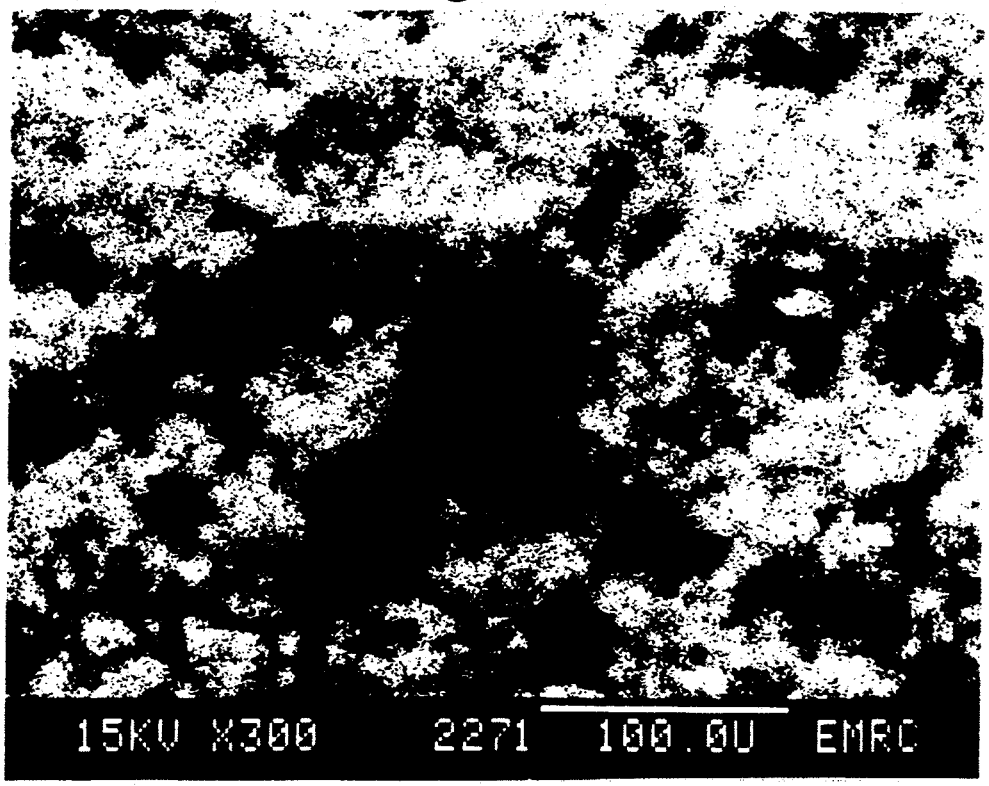
FIG. 1a is a scanning electron microscope (SEM) photograph showing the silicon distribution of a cross-section of an extrudate containing a physical mixture of alumina and an acid washed montmorillonite clay.

As stated, this invention relates to a composition, a method of preparing the composition, a catalyst using the composition, and a process using the composition. One necessary component of the composition of this invention is a clay. Both natural and synthetic clays may be used including but not limited to bentonite, sepiolite, laponite TM, vermiculite, montmorillonite, kaolin, palygorskite (attapulgus), hectorite, chlorite, beidellite, saponite and nontronite. Of the above clays Laponite TM is a synthetic hectorine clay manufactured by LaPorte Co. and having the chemical formula $Na_{0.58}Si_8Mg_{5.4}2Li_{0.58}F_{2.5}(OH)_{1.5}O_{20}$(Laponite-B TM or $Na_{0.4-6}Si_8Mg_{5.54}Li_{0.46}(OH)_4O_{20}$(Laponite-RD TM ). Montmorillonite hectorite, beidellite and saponite have synthetic analogs. As stated, these clays are composed of semi-crystalline aluminosilica layers held together by Van der Waals and electrostatic forces. The clays (both natural and synthetic analogs) may be used as they occur (or as synthesized) or they may be modified by exchanging with metals or introducing pillars between the layers to give pillared clays. Any of the clays, including all the ones enumerated above, may be exchanged with one or more metals selected from the group consisting of $Fe^{+3}$, $Cr^{+3}$, $Al^{+3}$, $Ti^{+4}$ and $Zr^{+4}$. The clays into which pillars may be introduced are the smectite clays (natural and synthetic) which are hectorite, beidellite, laponite TM, nontronite, saponite and montmorillonite. The pillars are selected from aluminum chlorohydrate (ACH) and rare earth ACH.

Aluminum chlorohydrate (also known as aluminum chlorohydroxide) is a polymeric metal complex having the empirical formula $$Al_{2+n}(OH)_{2n}Cl_6$$

where n has a value of about 4 to 12. The preparation of this aluminum polymer is generally known to those skilled in the art. See, for example: Tsuitida and Kobayashi, *J. Chem. Soc.* Japan (Pure Chem. Sect.), 64, 1268 (1943). Inoue, Osugi and Kanaji, *J. Chem. Soc.* Japan (Ind. Chem. Sec.), 61, 407 (1958).

A rare earth ACH is an ACH as described above which is modified to include one or more rare earth elements such as cerium, lanthanum, neodymium, europium, etc. The ACH polymer is modified with the rare earth by adding a soluble rare earth salt, preferably a water soluble rare earth salt. Examples of rare earth salts are the nitrates, halides, sulfates and acetates. Preferred rare earth elements are cerium and lanthanum with cerium nitrate and lanthanum nitrate being the preferred salts. The rare earth is introduced into the polymer or oligomer structure by mixing the rare earth salt either in solution (water preferred) or as a solid with the ACH. The mixture is refluxed at a temperature of about 105° to about 145° C. for a time of about 24 to about 100 hours. The weight ratio of rare earth(expressed as oxide, e.g., $CeO_2$) to alumina ($Al_2O_3$) in the solution prior to refluxing is from about 1:52 to about 1:1.

When these pillars are introduced into the clays, the clays are referred to as ACH clays and rare earth ACH, e.g., CeACH, clays. The ACH or rare earth ACH clays are prepared by means well known in the art such as adding the desired clay to an ACH or rare earth ACH solution, stirring, filtering, redispersing with water (one or more times), isolating, drying and calcining at about 500° to about 800° for a time sufficient to fix the structure (preferably about 16 hours). Any and all mixtures of the clays enumerated above can be used in the invention.

A second necessary component of the composition of this invention is an inorganic oxide matrix. The inorganic oxide may be selected from the group consisting of alumina, titania, silica, zirconia, $P_2O_5$ and mixtures thereof with alumina being preferred. The clay will be present in the inorganic oxide matrix in a concentration from about 5 to about 80 weight percent of the composition and preferably from about 30 to about 70 weight percent of the composition.

In addition to the composition containing a clay and an inorganic oxide matrix, it is necessary that the clay be homogeneously dispersed throughout the inorganic oxide matrix. By homogeneously dispersed is meant that the composition is homogeneous on a one micron scale, that is, if one looks at a one square micron area one will find a uniform distribution of matrix and clay components, i.e., there are no large, segregated, areas of one or the other component.

One can obtain such a homogeneous dispersion by using a sol of the element which is the precursor of the inorganic oxide. A sol or hydrosol is a solution which, when placed in a glass vessel between one's line of vision and a strong light source, shows a bluish cast. This is known as the Tyndall effect. By using a sol, the clay layers become totally surrounded by the sol such that upon further processing one obtains clay layers that are totally or completely surrounded by the inorganic oxide matrix. That is, one obtains a layered clay homogeneously dispersed in an inorganic oxide matrix.

A preferred method of obtaining such a dispersion involves modifying the well known oil drop method which is taught in U.S. Pat. No. 2,620,314 and which is incorporated by reference. For example, when alumina is the desired inorganic oxide, the modified oil drop method comprises forming an aluminum hydrosol by any of the techniques taught in the art and preferably by reacting aluminum metal with hydrochloric acid; adding the desired clay to the aluminum hydrosol; combining the resulting hydrosol mixture with a suitable gelling agent; and dropping the resultant mixture into an oil bath maintained at elevated temperatures. The droplets of the mixture remain in the oil bath until they set and form hydrogel spheres. The spheres are then continuously withdrawn from the oil bath and typically subjected to specific aging and drying treatments in oil and ammoniacal solution to further improve their physical characteristics. The resulting aged and gelled spheres are then washed and dried at a relatively low temperature of about 80°–150° C. and subjected to a calcination procedure at a temperature of about 455°–705° C. for a period of about 1 to about 20 hours. The treatment effects conversion of the hydrogel to the corresponding crystalline gamma-alumina matrix having the layered clay homogeneously dispersed therein.

Another method of homogeneously dispersing the clay in the inorganic oxide matrix is to form a mixture of a precursor sol or a precursor salt solution and a clay followed by spray drying the mixture to give particles containing homogeneously dispersed clay and finally calcining the particles to convert the sol or salt into the desired inorganic oxide.

The homogeneous dispersion described above cannot be obtained by spray drying (see U.S. Pat. No.

4,844,790) or extruding physical mixtures of the inorganic oxide and layered clay. When a slurry or dough is formed of the two components, one is using powders of the two components, whose particle sizes can range from 5 microns to 30 microns. Therefore, there will be 5 to 30 micron particles of one component separating particles of the other component. Although the final product will look homogeneous on a macroscopic scale, it will not be homogeneous on a microscopic scale as defined above. Additionally, since there is no sol to surround and separate the clay layers and keep them separated, upon calcining the clay layers are not completely surrounded by the inorganic oxide matrix.

Figure 1B:
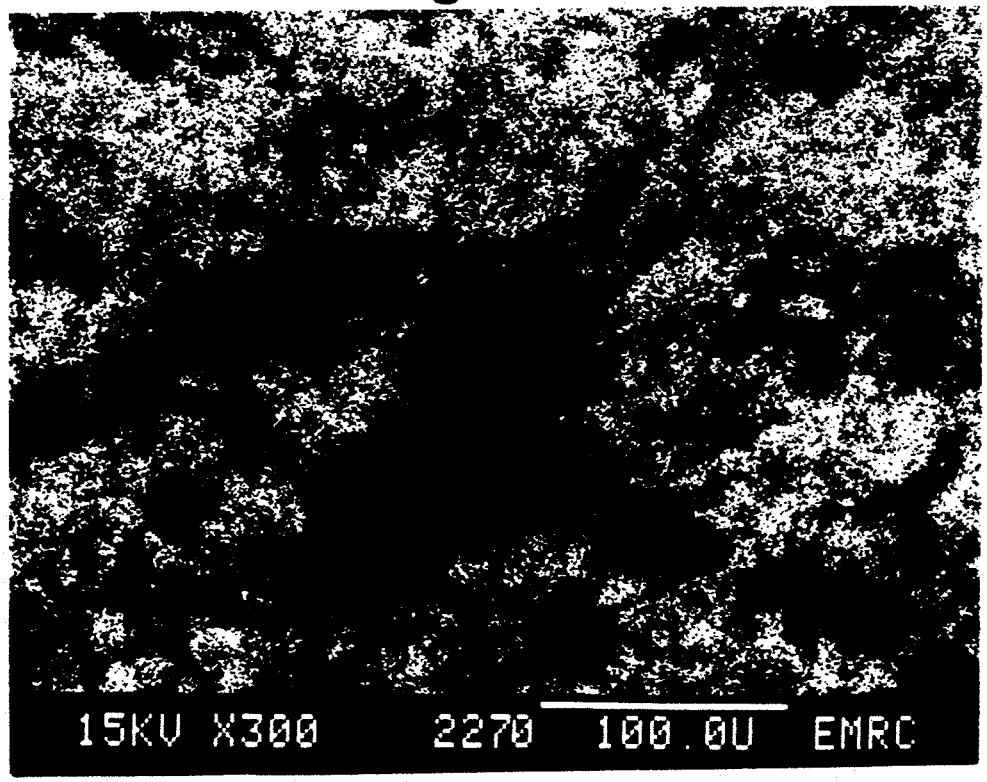
Figure 2A:
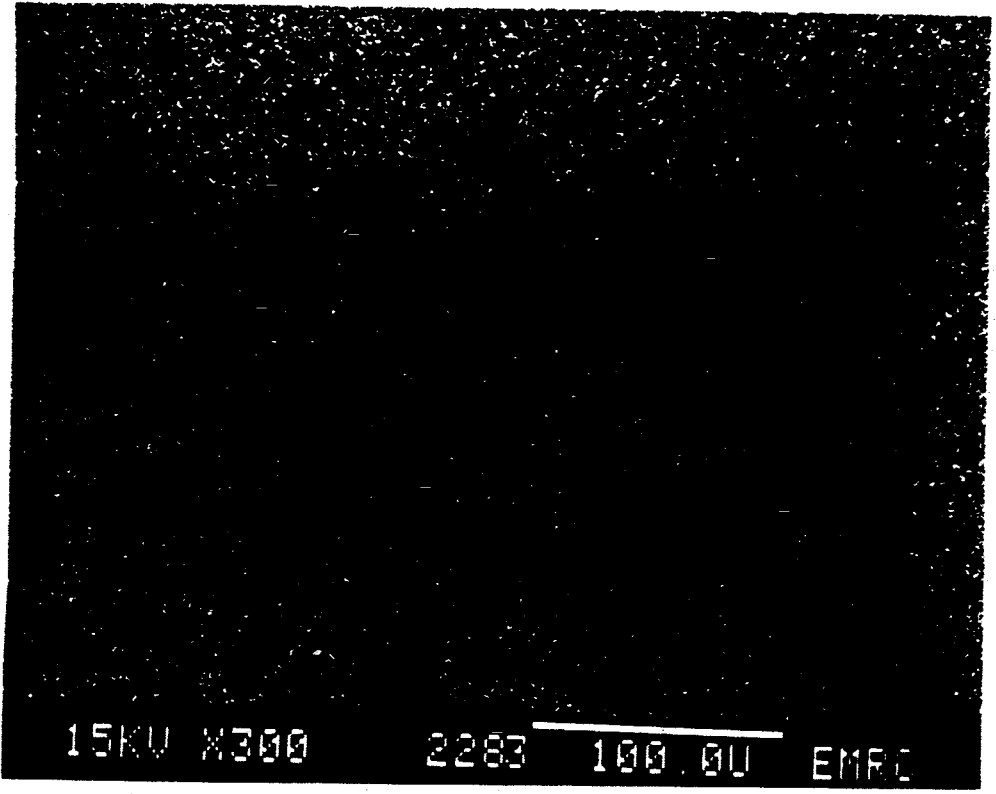
FIG. 2a is a SEM photograph showing the silicon distribution of a cross-section of a sphere containing alumina and an acid washed montmorillonite clay prepared according to the instant invention.
Figure 2B:
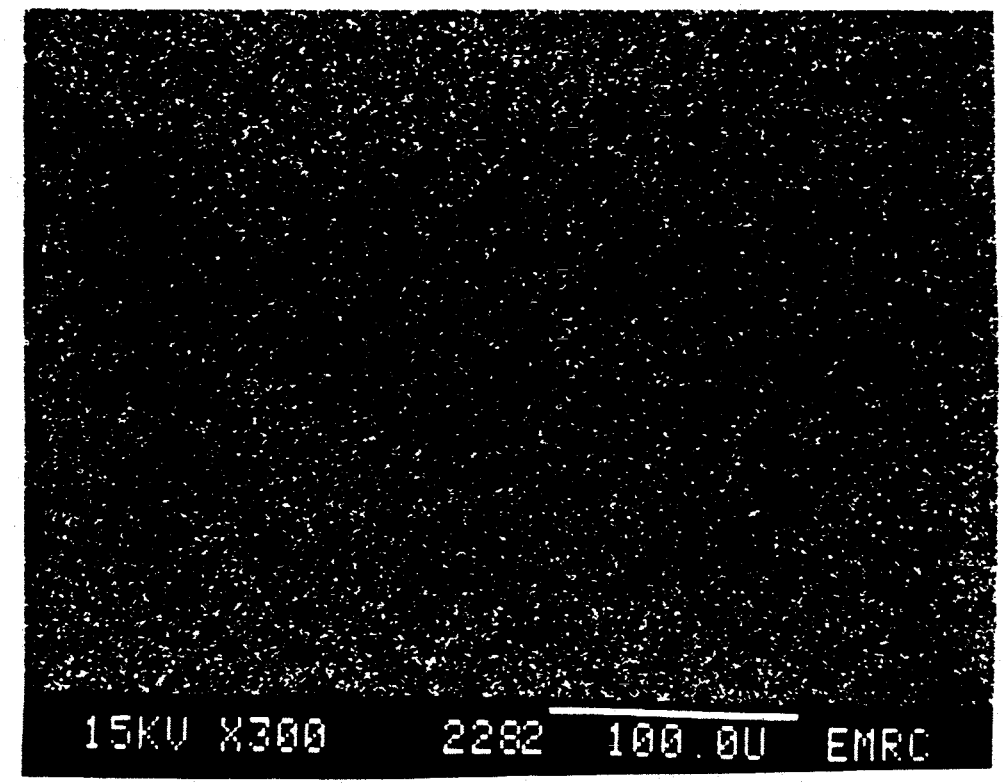

It is believed that it is the homogeneous dispersion of the clay in the oxide matrix which leads to the observed increase in activity. The homogeneous dispersion is illustrated by the SEM photographs presented in FIGS. 1 and 2. FIG. 1 presents two SEM cross-sectional photographs of an extrudate prepared as in Example 2, namely a physical mixture of Filtrol #24 and alumina. The bright spots in FIG. 1a indicate the presence of silicon, while the bright spots in FIG. 1b indicate the presence of aluminum. FIG. 2 presents two SEM cross-sectional photographs of a sphere prepared according to this invention and as described in Example 1. The clay used in this sample was Filtrol #24 and the matrix oxide was alumina. FIG. 2a is a silicon (bright areas) spot map, while FIG. 2b is an aluminum spot map of the cross-sectional area of a sphere. Since silicon is only found in the clay the more homogeneous the silicon spot map the greater the extent of the dispersion of the clay in the alumina matrix.

Looking at FIG. 1a one observes regions which are very intense and other regions which are less intense. This is evidence of inhomogeneous dispersion of the clay. The same pattern is observed for the aluminum distribution (FIG. 1b); that is, some areas are more intense than others. It is also observed that there are large voids probably formed by the packing of the two components. Further, certain areas that have intense aluminum spots do not have intense silicon spots and vice versa. Clearly this sample is not homogeneous.

In contrast to FIGS. 1a and 1b, FIGS. 2a and 2b are extremely homogeneous. For example the silicon spot map of FIG. 2a shows that the intensity of the spots is uniform throughout the whole area photographed. The aluminum spot map of FIG. 2b similarly shows that the intensity of the aluminum spots is uniform throughout the area photographed. Additionally, there is a correspondence of silicon intensity with aluminum intensity and whatever voids are present are uniformly distributed throughout the sample area. The homogeneity of this sample, prepared according to the instant invention, is therefore verified.

As will be shown in more detail and without wishing to be bound by any particular theory, the fact that the clay layers are surrounded by the inorganic oxide matrix leads to synergistic interaction between the clay and the inorganic oxide matrix, e.g., alumina. This synergistic effect gives rise to an increase in activity.

The composition which is derived from this invention is useful as a catalyst or as a support for metals which are themselves catalysts. Thus, without any further modifications, the composition of this invention can be used to catalyze reactions such as alkylation, cracking, oligomerization, isomerization and transalkylation. Additionally, a metal component (either as the metal or as the metal oxide) may be deposited on the composition to provide additional or different catalytic properties. The metal which makes up the metal component may be selected from the group consisting of the Group IIIA, IIIB, IVB, VIII metals, molybdenum, tungsten and mixtures thereof.

The metal component may be deposited on the composition, which acts as a support, in any suitable manner known in the art. One method involves impregnating the support with an aqueous solution of a decomposable compound of the metal or metals. By decomposable is meant that upon heating the metal compound is converted to the metal or metal oxide and the release of byproducts. Illustrative of the decomposable compounds of said metals are cobalt chloride, cobalt nitrate, cobalt acetate, cobalt sulfate, iron chloride, iron nitrate, iron acetate, iron sulfate, nickel chloride, nickel nitrate, nickel acetate, nickel sulfate, ammonium chloroplatinate, chloroplatinic acid, bromoplatinic acid, dinitrodiamino platinum, sodium tetranitroplatinate, rhodium trichloride, hexaamminerhodium chloride, rhodium carbonylchloride, sodium hexanitrorhodate, chloropalladic acid, palladium chloride, palladium nitrate, diamminepalladium hydroxide, tetraamminepalladium chloride, hexachloroiridate (IV) acid, hexachloroiridate (III) acid, ammonium hexachloroiridate (III), ammonium aquohexachloroiridate (IV), ruthenium tetrachloride, hexachlororuthenate, hexaammineruthenium chloride, osmium trichloride, ammonium osmium chloride, ammonium paramolybdate, ammonium tungstate, aluminum chloride, aluminum nitrate, boric acid, gallium nitrate, gallium trichloride, indium chloride, indium nitrate, thallium acetate, scandium nitrate, lanthanum chloride, lanthanum nitrate, yttrium chloride, yttrium nitrate, titanium trichloride, zirconium tetrachloride, zirconium sulfate, and hafnium chloride.

When more than one metal is desired, the metals can be in a common aqueous solution or in separate aqueous solutions. When separate aqueous solutions are used, impregnation of the support can be performed sequentially in any order. Although the concentration of metal component can vary substantially it is desirable that the catalyst contain a concentration of the metal component as the metal from about 0.1 to about 30 weight percent of the support and preferably from about 1 to about 15 weight percent.

A preferred impregnation procedure involves the use of a steam-jacketed rotary dryer. The support is immersed in the impregnating solution containing the desired metal compound contained in the dryer and the support is tumbled therein by the rotating motion of the dryer. Evaporation of the solution in contact with the tumbling support is expedited by applying steam to the dryer jacket. The resultant composite is allowed to dry under ambient temperature conditions, or dried at a temperature of about 80° to about 110° C., followed by calcination at a temperature of about 400° to about 650° C. for a time of about 1 to about 4 hours, thereby converting the metal compound to the metal or metal oxide.

As stated, the composition of this invention with or without an additional metal component can be used as an alkylation catalyst. The conditions necessary to carry out alkylation of aromatic compounds are well known and are disclosed, for example, in U.S. Pat. Nos. 3,965,043 and 3,979,331 which are incorporated by reference. Generally the process can be carried out in a batch type or a continuous type operation. In a batch type process, the catalyst, aromatic compound and alkylating agent are placed in an autoclave and the pressure increased, if necessary, in order to effect the reaction in the liquid phase. An excess amount of aromatic compound should be present, preferably in a range of about 2:1 to about 20:1 moles of aromatic compound per mole of alkylating agent. The reaction is carried out at an elevated temperature since the rate of alkylation is undesirably low at room temperature. Preferably the temperature is in the range of about 40° to about 200° C. The process is carried out for a time of about 0.5 to about 4 hours, after which the product is separated from the starting materials by conventional means.

If it is desired to carry out the process in a continuous manner, the catalyst is placed in a reactor which is heated to the desired operating temperature and the pressure increased above atmospheric, if necessary. The aromatic compound and alkylating agent are flowed over the catalyst bed at a predetermined liquid hourly space velocity sufficient to effect alkylation. The effluent is continuously withdrawn and conventional separation means used to isolate the desired product.

Additionally, the composition of this invention with or without additional catalytic metals or other catalytic materials such as Y zeolite may be used as a hydrocracking catalyst. Typically, hydrocracking conditions include a temperature in the range of 400° to 1200° F. (204°–649° C.), preferably between 600° and 950° F. (316°–510° C.). Reaction pressures are in the range of atmospheric to about 3,500 psig (24,132 kPa g), preferably between 200 and 3000 psig (1379–20,685 kPa g). Contact times usually correspond to liquid hourly space velocities (LHSV) in the range of about 0.1 $hr^{-1}$ to 15 $hr^{-1}$, preferably between about 0.2 and 3 $hr^{-1}$. Hydrogen circulation rates are in the range of 1,000 to 50,000 standard cubic feet (scf) per barrel of charge (189–8,888 std. $m^3/m^3$), preferably between 2,000 and 30,000 scf per barrel of charge (355–5333 std. $m^3/m^3$).

The following examples are presented in illustration of this invention and are not intended as undue limitations on the generally broad scope of the invention as set out in the appended claims.

EXAMPLE 1

Spheres containing a clay and an alumina matrix were prepared as follows. An aluminum hydrosol was prepared by reacting aluminum metal with hydrochloric acid to give a sol containing 12–13.5 weight percent aluminum and an Al to Cl ratio of 1.19. Filtrol #24 clay (an acid washed or activated montmorillonite clay obtained from Engelhard Corp.) was added to the sol to give 50% clay by weight (and 50% alumina) in the finished spheres. The clay was added to the hydrosol with vigorous mixing and then further mixed by using a ball mill. Hexamethylene tetrammine (HMT) was added to the mixture to gel the mixture into spheres when dropped through a tower of oil maintained at 95° C. The amount of HMT which was added was about 130% of the amount required to neutralize the acid in the aluminum sol.

After the spheres were removed from the hot oil, they were pressure aged at 140° C. for 2 hours and then washed with 10 liters of a dilute ammonium hydroxide solution (1 weight percent $NH_4OH$) dried at 110° C. and calcined at 650° C. for 2 hours. These spheres were designated sample A. After calcination, the cracking activity of the spheres was measured using the 1-heptene microreactor test described in Example 10. The results of this test are presented in Table 1.

EXAMPLE 2

A catalyst was prepared by forming a doughy paste from a powder containing 80% Filtrol #24 and 20% alumina and water. The paste was extruded through a die to form 1/16" extrudates which were then calcined in an air atmosphere containing 10% stream for 2 hours at 600° C. This catalyst was designated sample B and was also tested according to Example 10 and the results presented in Table 1.

EXAMPLE 3

Synthetic saponite was prepared by hydrothermal synthesis as described in U.S. Pat. No. 4,749,676 which is incorporated by reference. Magnesium sulfate, sodium aluminate and waterglass were used as the sources of the Mg, Al and Si respectively. The atomic ratio of (Na-Al): Mg+Si+3/2Al) in the gel was 0.34 which corresponds to a Si/Al ratio of 5.6 in the tetrahedral sheet. The gel pH was adjusted to 9 by adding NaOH and $Na_2CO_3$ and then the gel was placed in a Parr Bomb heated to 200° C. under autogenous pressure for 6 hours to crystallize the saponite. The product was recovered by filtration washed with deionized water and dried at 110° C. for 4 hours. The dried product was ground to a fine powder.

EXAMPLE 4

The saponite powder prepared in Example 3 was exchanged with aluminum chlorohydrate as follows. The saponite powder (clay) was suspended in a solution consisting of water and aluminum chlorohydrate. The aluminum chlorohydrate was obtained from Reheis as a 50% aqueous solution. After 30 minutes, the saponite clay was collected by filtration and washed with water until the wash water was free of chloride. The clay was dried at 110° C. for 2 hours and then calcined at 450° C. for 3 hours. This sample was designated sample C and was tested in the 1-heptene cracking test of Example 10 and the results are presented in Table 1.

EXAMPLE 5

This example presents the preparation of spheres using the aluminum chlorohydrate exchanged saponite of Example 4. The procedure detailed in Example 1 was used to prepare the spheres except that the saponite of Example 4 was used in place of the Filtrol #24 clay. These spheres were designated sample D. After calcination, these spheres were tested using the 1-heptene cracking test of Example 10 and the results are presented in Table 1.

EXAMPLE 6

Filtrol #24 was obtained from Engelhard Corp. as 40–60 mesh granules. This sample was designated sample E and tested according to Example 10. The results are presented in Table 1.

EXAMPLE 7

Alumina spheres were prepared according to the procedure of Example 1 except that no clay was added to the alumina sol. These spheres were designated sample F and tested according to Example 10. These results are presented in Table 1.

EXAMPLE 8

A cerium-aluminum chlorohydrate pillared montmorillonite was prepared according to the procedure set forth in International Pat. No. WO 88/06488. After drying, the pillared clay was steamed at 650° C. for 3 hours. This sample was designated sample G and was tested in the 1-heptene cracking test of Example 10. The results are presented in Table 1.

EXAMPLE 9

This example presents the preparation of spheres using the Ce-aluminum chlorohydrate pillared clay of Example 8. The procedure detailed in Example 1 was used to prepare the spheres except that the pillared clay of Example 8 was used in place of the Filtrol #24 clay. These spheres were designated sample H. After calcination, these spheres were tested using the 1-heptene cracking test of Example 10 and the results are presented in Table 1.

EXAMPLE 10

Heptene Cracking Test

The following test procedure was used to evaluate the materials prepared in Examples 1-5. The heptene cracking test or the microreactor cracking test uses an electrically heated reactor which is loaded with 125 mg of 40-60 mesh (420-250 microns) particles of the catalyst to be tested. Each catalyst was dried in situ for 30 minutes at 200° C. using flowing hydrogen, and then subjected to a reduction treatment of 425° C. in flowing hydrogen for one hour. The temperature of the reactor was then adjusted to 425° C. (inlet). The feed stream used to test the catalyst consists of hydrogen gas which is saturated with 1-heptene at 0° C. and atmospheric pressure. The feed stream was flowed over the catalyst at a flow rate of 125 cc/min. The effluent gas stream was analyzed using a gas chromatograph. What is reported in the examples that follow is the total conversion of 1-heptene to cracked products. The results from all the tests is presented in Table 1.

TABLE 1

| Sample I.D. | Cracking (% Conv.) |
| --- | --- |
| A (50% Filtrol #24/50% Al$_2$O$_3$ prepared by oil dropping) | 20 |
| B (80% Filtrol #24/20% Al$_2$O$_3$ as extrudates) | 7 |
| C (100% Saponite) | 56 |
| D (30% saponite/70% Al$_2$O$_3$ by oil dropping) | 25 |
| E (Filtrol #24, 100%) | 25 |
| F (Al$_2$O$_3$ spheres) | 3 |
| G (CeACH montmorillonite) | 2 |
| H (CeACH clay/Al$_2$O$_3$ spheres) | 13 |

The data show several important features. First, the activity of sample A which was prepared by oil dropping a mixture of Filtrol #24 clay and alumina is greater than would be expected from a physical mixture of clay and alumina. Indeed, an extruded sample of 80% Filtrol #24 and 20% alumina (sample B) shows much poorer activity than the oil dropped sample.

Second, a comparison of the results for samples C, D and F shows that an intimate mixture of a saponite clay (30%) and alumina (70%) has greater activity than would be expected from a physical mixture of the saponite and alumina. Finally, samples G and H show the same effect, that is, when a CeACH clay is tested alone (sample G) very little activity is observed, whereas when the clay is dispersed in an alumina matrix, a significant increase in activity is observed. Therefore, dispersing a clay in an alumina matrix gives rise to synergistic effects which increases the activity of the composition versus a physical mixture of the clay and alumina.

Thus, having described the invention in detail, it will be understood by those skilled in the art that certain variations and modifications may be made without departing from the spirit and scope of the invention as defined herein and in the appended claims.

We claim as our invention:

1. A composition consisting essentially of a layered clay homogeneously dispersed in an inorganic oxide matrix, such that the clay layers are completely surrounded by the inorganic oxide matrix, the inorganic oxide selected from the group consisting of alumina, titania, silica, zirconia, P$_2$O$_5$ and mixtures thereof.

2. The composition of claim 1 where the clay is present in a concentration from about 5 to about 80 weight percent of the composition.

3. The composition of claim 1 where the clay is present in a concentration from about 30 to about 70 weight percent of the composition.

4. The composition of claim 1 where the inorganic oxide is alumina.

5. The composition of claim 1 where the clay is selected from the group consisting of bentonite, vermiculite, montmorillonite, kaolin, sepiolite, palygorskite, hectorite, chlorite, beidellite, saponite, nontronite and mixtures thereof.

6. The composition of claim 5 where the clay is montmorillonite and is present in a concentration from about 5 to about 80 weight percent of the composition.

7. The composition of claim 1 where the clay is a pillared clay selected from the group consisting of aluminum chlorohydrate (ACH) clay and rare earth ACH clay, the clay selected from the group consisting of hectorite, beidellite, nontronite, saponite, montmorillonite and mixtures thereof.

8. The composition of claim 7 where the pillared clay is a rare earth ACH clay.

9. The composition of claim 8 where the rare earth ACH clay is a cerium ACH clay.

10. A catalyst comprising a support having dispersed thereon a metal component selected from the group consisting of a Group IIIA, IIIB, IVB, VIII metal, molybdenum, tungsten and mixtures thereof, the support consisting essentially of a layered clay homogeneously dispersed in an inorganic oxide, such that the clay layers are completely surrounded by the inorganic oxide matrix, the inorganic oxide selected from the group consisting of alumina, titania, silica, zirconia, P$_2$O$_5$ and mixtures thereof.

11. The catalyst of claim 10 where the metal component is present on the support in an amount from about 1 to about 30 weight percent (as the metal) of the support.

12. The catalyst of claim 10 where the inorganic oxide is alumina.

13. The catalyst of claim 10 where the metal component is a mixture of nickel and tungsten.

14. The catalyst of claim 10 where the clay is selected from the group consisting of bentonite, vermiculite, montmorillonite, kaolin, sepiolite, palygorskite, hectorite, chlorite, beidellite, saponite, nontronite and mixtures thereof.

15. The catalyst of claim 14 where the clay is montmorillonite and is present in a concentration from about 5 to about 80 weight percent of the composition.

16. The catalyst of claim 10 where the clay is a pillared clay selected from the group consisting of aluminum chlorohydrate (ACH) clay and rare earth ACH clay, the clay selected from the group consisting of hectorite, beidellite, nontronite, saponite, montmorillonite, and mixtures thereof.

17. The catalyst of claim 16 where the pillared clay is a rare earth ACH clay.

18. The catalyst of claim 17 where the rare earth ACH clay is a cerium ACH clay.

19. The catalyst of claim 10 where the clay is present in a concentration from about 5 to about 80 weight percent of the support.

20. The catalyst of claim 10 where the clay is present in a concentration from about 30 to about 70 weight percent of the support.

21. A process of preparing a composition consisting essentially of a layered clay homogeneously dispersed in an inorganic oxide matrix, the process comprising mixing a clay with a hydrosol of a precursor of the inorganic oxide, forming spherical particles from said clay containing hydrosol and calcining said particles to form a composition comprising a clay homogeneously dispersed in an inorganic oxide matrix, such that the clay layers are completely surrounded by the inorganic oxide matrix.

22. The process of claim 21 where the inorganic oxide is selected from the group consisting of alumina, titania, silica, zirconia, $P_2O_5$ and mixtures thereof.

23. The process of claim 22 where the inorganic oxide is alumina.

24. The process of claim 21 where the clay is present in a concentration from about 5 to about 80 weight percent of the composition.

25. The process of claim 21 where the clay is selected from the group consisting of bentonite, vermiculite, montmorillonite, kaolin, sepiolite, palygorskite, hectorite, chlorite, beidellite, saponite, nontronite and mixtures thereof.

26. The process of claim 21 where the clay is a pillared clay selected from the group consisting of aluminum chlorohydrate (ACH) clay and rare earth ACH clay, the clay selected from the group consisting of hectorite, beidellite, nontronite, saponite, montmorillonite, and mixtures thereof.

27. The process of claim 26 where the pillared clay is a rare earth ACH clay.

28. The process of claim 27 where the rare earth ACH clay is a cerium ACH clay.

* * * * *